United States Patent [19]
Verheijen

[11] Patent Number: 5,811,252
[45] Date of Patent: Sep. 22, 1998

[54] MODIFIED PROENZYMES AS SUBSTRATES FOR PROTEOLYTIC ENZYMES

[75] Inventor: Johan Hendrikus Verheijen, Rodenrijs, Netherlands

[73] Assignee: Nederlandse Organisatie voor toegepast-natuurwetenschappelijk Onderzoek TNO, Netherlands

[21] Appl. No.: 499,048

[22] Filed: Jul. 6, 1995

[30] Foreign Application Priority Data

Jul. 7, 1994 [EP] European Pat. Off. .............. 94201966

[51] Int. Cl.$^6$ .............................. C12Q 1/37; C12Q 1/00; C12N 9/66; A61K 38/00
[52] U.S. Cl. ............................ 435/23; 435/24; 435/212; 435/215; 435/217; 435/218; 435/219; 435/4; 435/183; 435/975; 435/970; 435/968; 530/300; 530/333; 530/827
[58] Field of Search ................................ 435/23, 183, 24, 435/968, 212, 287, 215, 217, 218, 4, 219, 975, 970; 530/300, 333, 827

[56] References Cited

U.S. PATENT DOCUMENTS

| | | | |
|---|---|---|---|
| 4,448,715 | 5/1984 | Ryan et al. | 435/13 |
| 4,753,879 | 6/1988 | Rosa et al. | 435/212 |
| 5,094,953 | 3/1992 | Anderson et al. | 435/212 |
| 5,157,019 | 10/1992 | Glover et al. | 530/300 |
| 5,219,569 | 6/1993 | Blaber et al. | 435/23 |

OTHER PUBLICATIONS

Umeko Sema, et al; Difference Between Human and Guinea Pig Hageman Factors in Activation by Bacterial Proteinases: Cleavage Site Shift Due to Local Amino Acid Substitutions may Determine the ActivationEfficiency of Serine Proteinase Zymogens; Biochimica et Biophysica Acta 1180 (1993) pp. 267–276, Month Not Available.

J.H.Verheijen, et al; A Simple, Sensitive Spectrophotometric Assay for Extrinsic (Tissue–Type) Plasminogen Activator Applicable to Measurements in Plasma; Thrombosis and Haemostasis, Journal of the International Society on Thrombosis and Haemostasis; vol. 48, No. 3, Mar. 1982; pp. 266–269.

Jean Claude Drapier, et al; Regulation of Plasminogen Activator Secretion in Mouse Peritoneal Macrophages; Biochimie, vol. 61, No. 4, Apr. 1979, pp. 463–471.

Jan Pohl, et al; Chromophoric Peptide Substrates for Activity Determination of Animal Aspartic Proteinase in the Presence of Their Zymogens: A Novel Assay; Analytical Biochemistry, vol. 133, No. 1, Aug. 1983; pp. 104–108.

Bernard Le Bonniec, et al; Glu–192→Gln Substitute in Thrombin Mimics the Catalytic Switch Induced by Thrombomobulin; Proc. Natl. Acad. Sci. USA vol. 88 Aug. 1991, pp. 7371–7375.

Willem Stevens, et al; Structural Changes in the Protease Domain of Prothrombin Upon Activation as Assessed by N–Bromosuccinimide Modification of Trypophan Residues in Prethrombin–2 and Thrombin; Biochemistry, vol. 32, 1993 p. 2787–294, Month not available.

(List continued on next page.)

Primary Examiner—Louise Leary
Attorney, Agent, or Firm—Londa and Traub LLP

[57] ABSTRACT

Detection or determination of a protease in a sample by incubating the sample with a substrate of the protease and observing proteolytic cleavage of said substrate. The substrate is a modified proenzyme containing a recognition site, e.g., an activation site, cleavable by said protease. Proteolytic cleavage of the modified proenzyme is detected by observing the resulting activity using a suitable substrate of the activated proenzyme. The protease may be e.g. an aspartic protease or a metalloprotease, and the modified proenzyme e.g. pro-urokinase having a mutant activation site which is cleavable by the protease to be determined.

30 Claims, 11 Drawing Sheets

OTHER PUBLICATIONS

Francisco Burgos, et al; Analysis of the Activation Process of Porcine Procarboxypeptidase B and Determination of the Sequence of Its Activation Segment; Biochemistry, vol. 30, 1991; pp. 4082–4089, Month Not Available.

Yasunori Okada, et al; Matrix Metalloproteinsase 9 (92–kDa Gelatinese/Type IV Collagenase) from HT 1080 Human Fibrosarcoma Cells; The Journal of Biological Chemistry, vol. 267, No. 30, Oct. 25, 1992; pp. 2172–21719.

SEQUENCE LISTING ( 1 ) GENERAL INFORMATION:

( i i i ) NUMBER OF SEQUENCES: 9

( 2 ) INFORMATION FOR SEQ ID NO: 1:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO: 1:

Arg Pro Leu Gly Ile Ile Gly Gly
        1                    5

( 2 ) INFORMATION FOR SEQ ID NO: 2:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: other nucleic acid ( i i i ) HYPOTHETICAL: NO ( x i ) SEQUENCE DESCRIPTION: SEQ ID NO: 2:

TAGCGCCCCG GGCTCGCCAC CAT    23

( 2 ) INFORMATION FOR SEQ ID NO: 3:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid ( i i i ) HYPOTHETICAL: NO ( x i ) SEQUENCE DESCRIPTION: SEQ ID NO: 3:

ACGGGTCTGG GGAGACCGGT    20

( 2 ) INFORMATION FOR SEQ ID NO: 4:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: other nucleic acid ( i i i ) HYPOTHETICAL: NO ( x i ) SEQUENCE DESCRIPTION: SEQ ID NO: 4:

AGCTTCCCGG GAGGCCTGTC GACA    24

( 2 ) INFORMATION FOR SEQ ID NO: 5:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: other nucleic acid ( i i i ) HYPOTHETICAL: NO ( x i ) SEQUENCE DESCRIPTION: SEQ ID NO: 5:

GATCTGTCGA CAGGCCTCCC GGGA    24

( 2 ) INFORMATION FOR SEQ ID NO: 6:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: other nucleic acid ( i i i ) HYPOTHETICAL: NO ( x i ) SEQUENCE DESCRIPTION: SEQ ID NO: 6:

-continued

CGGCGGCTCG GGATTATTGG GGGAGAATTC ACC                             33

( 2 ) INFORMATION FOR SEQ ID NO: 7:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( x i ) SEQUENCE DESCRIPTION: SEQ ID NO: 7:

CCCGAGCGGC CGCCTCAGAG TCTTTTGGCC ACA                              33

( 2 ) INFORMATION FOR SEQ ID NO: 8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( x i ) SEQUENCE DESCRIPTION: SEQ ID NO: 8:

ATTATTGGGG GAGAATTCAC C                                           21

( 2 ) INFORMATION FOR SEQ ID NO: 9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( x i ) SEQUENCE DESCRIPTION: SEQ ID NO: 9:

CCTCAGAGTC TTTTGGCCAC A                                           21

MODIFIED PROENZYMES AS SUBSTRATES FOR PROTEOLYTIC ENZYMES

FIELD OF THE INVENTION

This invention is in the field of determining the presence or amount of a proteolytic enzyme in a sample and concerns both an assay process and an assay kit and device therefor.

BACKGROUND OF THE INVENTION

Proteolytic enzymes catalyze the hydrolysis of peptide bonds in proteins or peptides. These enzymes widely occur in nature from micro-organisms to man and have many different functions. They are involved in digestive processes, both on the level of the organism [digestive tract enzymes e.g. pepsin, (chymo)trypsin] and individual cells (lysosomal enzymes e.g. cathepsins). They play a role in invasive behaviour of both micro-organisms and cells in multicellular organisms and in the latter are involved in growth and development (e.g. plasminogen activators, collagenases). Besides these obvious processes proteolytic enzymes play critical roles in regulatory networks such as blood coagulation and fibrinolysis, blood pressure regulation and activation of growth factors and prohormones.

Apart from these (patho)physiological functions proteolytic enzymes are increasingly used in biotechnology ranging from pharmaceutical synthesis to preparation of food (e.g. cheese) and on a very large scale in detergents for general use.

All proteolytic enzymes catalyze the same basic reaction:

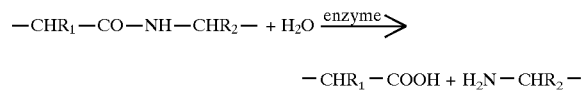

i.e. an amide bond hydrolysed under mild conditions, typically pH between 5–8 and temperature of 25°–37° C. Without enzymes much harsher conditions, such as boiling in 6 M hydrochloric acid, are required. The difference between enzymatic and non-enzymatic cleavage of peptide bonds is not only a matter of conditions, enzymatic processes are much faster and can be very selective. Examples are known in which only one specific protein within a mixture is hydrolyzed and sometimes even only one specific peptide bond within one such a protein is attacked. The general idea about enzymatic hydrolysis of peptide bonds is that an enzyme contains an active site, typically involving 2–3 amino acid residues, directly involved in the reaction and sometimes additional substrate recognition sites not involved in the hydrolysis reaction but conferring specificity to the enzyme.

At this moment four different classes of proteolytic enzymes are known, differing in the mechanism of the reaction and the amino acid residues involved in catalysis (Table 1).

TABLE 1

Classes of proteases

| name | EC number | active site | | |
|---|---|---|---|---|
| serine proteases | 3.4.21 | Ser | His | Asp* |
| cysteine proteases | 3.4.22 | Cys | His | Asp* |
| aspartic proteases | 3.4.23 | Asp | Asp | |
| metalloproteases | 3.4.24 | His | His | $Zn^{2+}$ |

*Asp not always present

Within each class, enzymes having different substrate specificities and properties occur. Many proteolytic enzymes can occur in an inactive proenzyme form. In many cases proenzyme activation is itself a proteolytic process. In this way positive or negative feedback regulation can occur, which is essential for regulation of proteolytic cascades like blood coagulation.

Due to their involvement in many (patho)physiological processes proteolytic enzymes play a role in many diseases and measurement of the activity of certain enzymes can be important for diagnosis (Table 2).

TABLE 2

Some clinically important proteases

| enzyme | involved in | clinical phenomenon as result of defect |
|---|---|---|
| factor VIIa | blood clotting | bleeding/thrombosis |
| factor IXa | blood clotting | bleeding/thrombosis |
| factor Xa | blood clotting | bleeding/thrombosis |
| APC | blood clotting | bleeding/thrombosis |
| thrombin | blood clotting | bleeding/thrombosis |
| t-PA | fibrinolysis/extra-cellular proteolysis | bleeding/thrombosis/invasion |
| u-PA | fibrinolysis/extra-cellular proteolysis | bleeding/thrombosis/invasion |
| plasmin | fibrinolysis/extra-cellular proteolysis | bleeding/thrombosis/invasion |
| trypsin | digestive tract | pancreatitis |
| chymotrypsin | digestive tract | pancreatitis |
| enterokinase | digestive tract | pancreatitis |
| pepsin | digestive tract | pancreatitis |
| cathepsin B,H,L,S,D | lysosomal digestion | |
| cathepsin G | | lung emphysema |
| renin | blood pressure regulation | blood pressure problems |
| angiotensin converting enzyme | blood pressure regulation | blood pressure problems |
| matrix metalloproteases (collagenases, stromelysins, gelatinases) | invasion, cell migration | cancer, invasion, rheumatoid arthritis, inflammation |
| macrophage elastase | | |
| C1r | complement system | inflammation, rheumatoid arthritis |
| C1s | | inflammation, rheumatoid arthritis |

Activity measurements of clinically important proteolytic enzymes are in general use. Especially for a number of key enzymes involved in the coagulation and fibrinolysis cascades, assays have been developed.

Measurement of enzymatic activity using the natural substrate is not always possible, or leads to elaborate complicated assays not suitable for routine application. The development of peptide synthesis has led to the use of synthetic peptides as substrates for proteolytic enzymes. Especially for many serine proteases chromogenic or fluorogenic peptide substrates have been devised which are often commercially available. Development of such substrates for serine proteases is relatively easy since these enzymes do not recognize the sequence which is C-terminal ($P_1^\triangledown$-$P_2^{\triangledown\text{-}P}{}_3^\triangledown$) to the hydrolyzed bond (FIG. 1). This part can be replaced by a chromogenic or fluorogenic leaving group like p-nitroaniline or β-naphtylamine. Upon this principle many commercially available substrates and assay kits are based and assays based on these methods can readily be automated. In many cases the specificity and sensitivity obtained with these peptide substrates is high enough to enable detection and quantification of physiological concentrations of enzymes in biological fluids or tissue-extracts. Sometimes the sensitivity can be further increased by employing two coupled reactions as has been described for plasminogen activators (Drapier et al. (1979) Biochimie 61, 463–471).

Measurement of metalloproteases and aspartic proteases is much more difficult due to some particular characteristics of these enzymes. In general these enzymes, unlike serine proteases, recognize the amino acid sequence on both sides of the bond to be split ($P_3$-$P_2$-$P_1$-$P_1^\nabla$-$P_2^\nabla$-$P_3^\nabla$) (FIG. 1). Thus, substrates where a non-peptide bond is split, such as the chromogenic or fluorogenic substrates used for determination of serine proteases cannot be employed for determination of metalloproteases or aspartic proteases. Two different synthetic substrate types exist nowadays for these enzymes: (1) peptides containing only the necessary recognition sequences for the protease. In this case hydrolysis is followed by a physico-chemical separation technique like HPLC. (2) Peptides containing besides the recognition sequence also a potential fluorescent group together with a quenching group. When both groups are in close proximity, fluorescence is quenched. Fluorescence is only observed after hydrolysis of the peptide and subsequent loss of quenching. Substrates belonging to the first group have been described for a number of interesting enzymes. Assays based on them are generally elaborate, difficult to perform and to automate, thus preventing their use in routine (clinical) applications. The second, internally fluorescent quenched type of substrate is much more attractive than the first, since detection is much easier and simpler to be automated. For routine purposes, however, detection using a colour change instead of fluorescence change would be very desirable, since most current laboratory automation equipment is based on such technology. In the present invention principles are described to determine proteolytic enzymes which only recognize and hydrolyze bonds between two aminoacid residues with equipment generally present in clinical or biochemical laboratories.

SUMMARY OF THE INVENTION

The invention provides a method of determining a protease, or its precursor after activation, in a sample, comprising incubating the sample with a substrate of said protease and determining proteolytic cleavage of said substrate, wherein said substrate is a modified proenzyme containing a recognition site which is cleavable by said protease. Said recognition site may be an activation site, i.e. a site whose cleavage results in the formation of active enzyme. Alternatively, said recognition site may be a site whose cleavage converts the proenzyme into a substrate for an other enzyme which is capable of activating the proenzyme. Proteolytic cleavage of said modified proenzyme may be determined by observing or measuring the resulting activity using a suitable substrate of the activated proenzyme. The sample will usually be a biological sample, such as a biological fluid, a fraction of a biological fluid, a biological tissue, an extract of a biological tissue, and a fraction of an extract of a biological tissue. The modified proenzyme may be derived from a proenzyme by providing it with a recognition site cleavable by the protease to be determined. In particular, said modified proenzyme may be derived from a proenzyme by replacing its activation site by an activation site which is cleavable by the protease to be determined.

The invention also provides the modified proenzyme per se, more particularly a modified proenzyme derived from a proenzyme by replacing its activation site by an activation site which is cleavable by a protease different from the one which activates the unmodified proenzyme.

The invention further provides a kit for determining a protease, or its precursor after activation, in a sample, comprising a modified proenzyme as defined herein, together with at least one member from the group consisting of substrates for activated proenzyme, secondary enzymes, buffer solutions, standard preparations, specific antibodies, microtiter plates, and instructions for use; and provides a device for determining a protease, or its precursor after activation, in a sample, comprising a modified proenzyme as defined herein.

DETAILED DESCRIPTION OF THE INVENTION

The invention can be used to determine catalytically active proteases involved in biotechnologically or (patho) physiologically interesting processes. The phrase "determining a protease" means both qualitative analysis, i.e. detecting the presence of the protease, determining whether it is present, and quantitative analysis, i.e. quantifying the protease, determining the protease activity present in the sample.

Examples of such proteases or proteolytic enzymes are given in Table 2. In contrast to existing methods the invention discloses methods equally potent to assay members of the serine or cysteine protease families or members of the aspartic protease or metalloprotease families which are much more difficult to determine. In many cases proteases do not occur in biological fluids in the catalytically active form but in an inactive zymogen form. In such cases conversion to the active form is required before the measurement. Depending on the zymogen, conversion to the active protease can be accomplished by limited proteolytic digestion, treatment with certain chemicals or mild denaturation by application of heat or sodium dodecylsulphate. Methods based on the invention can be very sensitive and specific and can easily be adapted for automation using generally available laboratory equipment. The invention appears to be most applicable in biotechnology, animal or human health research laboratories and hospitals and clinical laboratories. Other applications might be in quality control in pharmaceutical or food-processing industries.

The invention uses a proenzyme which can be converted to an active enzyme by one or more specific proteolytic events. Subsequently the activity of the active enzyme is detected using existing methodology (FIG. 2). Such proenzymes exist in nature: pro-urokinase-type plasminogen activator, plasminogen and many of the coagulation factors are in fact such proenzymes. Activation of these natural proenzymes is in general only possible by the action of one or very few specific enzymes, generally the ones which are also physiologically involved in the activation of the particular proenzymes. Examples of particular proenzymes and their activation sequences are given in Table 3.

TABLE 3

Examples of suitable proenzymes

| proenzyme | bond split upon activation |
|---|---|
| prophospholipase A2 (human pancreas) | Ser-Pro-Arg ↑Ala-Val-Trp-Gln |
| prothrombin | Glu-Gly-Arg ↑Ile-Val-Glu-Gly |
| pro-urokinase | Arg-Phe-Lys ↑Ile-Ile-Gly-Gly |
| trypsinogen | Asp-Asp-Lys ↑Ile-Val-Gly-Gly |
| chymotrypsinogen | Leu-Ser-Arg ↑Ile-Val-Asn-Gly |
| pro-elastase | Val-Tyr-Arg ↑Val-Val-Gly-Gly |
| pro-subtilisin | Ala-Gly-Lys ↑Ser-Asn-Gly-Glu |
| coagulation factor V | Gly-Ile-Arg ↑Ser-Phe-Arg-Phe |
| coagulation factor VII | Pro-Gln-Arg ↑Ile-Val-Gly-Gly |
| coagulation factor IX | Asp-Phe-Thr-Arg ↑Val-Val-Gly-Gly |

TABLE 3-continued

Examples of suitable proenzymes

| proenzyme | bond split upon activation |
| --- | --- |
| coagulation factor X | Asn-Leu-Thr-Arg ↑Ile-Val-Gly-Gly |
| coagulation factor XII | Ser-Met-Thr-Arg ↑Val-Val-Gly-Gly |
| coagulation factor XI | Ile-Lys-Pro-Arg ↑Ile-Val-Gly-Gly |
| kallikrein | Thr-Ser-Thr-Arg ↑Ile-Val-Gly-Gly |
| plasminogen | Pro-Gly-Arg ↑Val-Val-Gly-Gly |
| cathepsin G | Ala-Gly-Glu ↑Ile-Ile-Gly-Gly |

Sequences obtained from SWISS-PROT, GenBank or PIR databases.

The proenzymes/enzymes used for the assay might be proteolytic enzymes themselves but this is not a necessity as long as the conversion of proenzyme into active enzyme is a proteolytic process. Phospholipase A2, an esterase involved in lipid degradation, is a typical example of a non-protease activated by a protease. Assays based on the principle of proteolytic activation of a proenzyme are known. A typical example is the determination of tissue-type plasminogen activator via activation of the proenzyme plasminogen, in this case also its natural substrate, followed by measurement of the resulting active plasmin by established procedures (Verheijen et al. (1982) Thromb. Haemostas. 48, 266–269). Due to the extreme specificity criteria of the activation reaction and the limited availability of suitable natural proenzymes, application of this principle is in general limited.

The present invention discloses modified, not naturally occurring, proenzymes, which can be activated by other proteases than the ones involved physiologically in their activation, thus extending the principle of measurement of a protease by proteolytic activation of a proenzyme to many more proteases. Activation of a proenzyme to an active enzyme often involves specific limited proteolysis at a particular site in the peptide sequence of the proenzyme. The actual amino acid sequence around the cut-site is most often responsible for the specificity of the activation reaction. The two polypeptide chains formed after activation remain in some cases connected by a disulfide bridge (as shown in FIG. 3), but this is not necessarily the case, and non covalent interactions and complete loss of the activation peptide do occur.

The present invention discloses proenzymes having a modified amino acid sequence around the activation cut-site. The modification can be chosen such that a specific protease or a group of proteases with a certain substrate specificity can cut the new sequence thus giving rise to an active enzyme which can be detected using established methods. The modified proenzyme is derived from a proenzyme which, in its unmodified form, is not a substrate of the protease to be determined. Due to the modification of the proenzyme, it is transformed into a substrate of the protease to be determined. Usually, the modification affects the interaction between the proenzyme and the protease(s) which are physiologically involved in its activation. Preferably, the modification is such that the modified proenzyme cannot be activated by the protease(s) which are physiologically involved in the activation of the unmodified proenzyme.

Apart from modifications around the activation site other secondary modifications might be present. Such secondary modifications could be directed on improving the properties of the proenzyme for the particular application. Useful secondary modifications include modifications increasing the (thermal) stability of the proenzyme, conferring resistance to other proteases than the target protease for the assay, conferring resistance to (naturally) occurring inhibitors, conferring reactivity to certain antibodies or ligands, aiding expression or purification etc. In most cases these secondary modifications are in other parts of the proenzyme and not near the activation cut site.

Many proenzymes potentially can be used for modification. It is particularly advantageous when the ratio of enzyme/proenzyme activity is high, the specificity of the active enzyme narrow and a suitable sensitive and simple assay principle for the activated enzyme exists. Particularly suitable could be members of the serine protease family. Many of these enzymes occur in proenzyme form and display an enormous increase in activity upon activation. Furthermore, for many of these enzymes simple, sensitive and specific assays exist including spectrophotometric or fluorimetric assays. Examples of suitable proenzymes and their natural activation sequence can be found in Table 3. The proenzyme is not necessarily a serine protease, other proteases or even other non-proteolytic enzymes can be used, provided that the conversion of the proenzyme to the active enzyme is a specific proteolytic process; an example is pro-phospholipase, a lipid degrading esterase.

A particular modification of the assay principle involves the application of a secondary enzyme to activate the modified proenzyme in two consecutive steps. In a first step the protease to be determined splits a bond in the modified proenzyme at some (small) distance away from its activation cleavage site. The resulting split modified proenzyme is not yet enzymatically active but has the potency to be activated by a secondary enzyme such as a peptidyldipeptidase. The action of the latter enzyme leads to activation. An important advantage of this embodiment of the invention is a greater versatility in the choice of the sequence to be recognized by the protease to be assayed, since its cleavage site does not have to be involved in proenzyme activation directly.

Such a situation occurs e.g. for the enzymes MMP-2 (gelatinase A), MMP-3 (stromelysin) and angiotensin converting enzyme. The respective substrate preferences ↑GluArg, ↑PheTrp and ↑GlyGly in the C-terminal part of the site of hydrolysis differ considerably from the activation recognition site as occurring in many proenzymes and in pro-urokinase in particular (↑IleIleGlyGly). In this case modified pro-enzymes suitable for indirect activation are most useful.

The following sequences: ProLeuGly↑$^1$GluArg↑$^2$IleGlyGly, ProLeuGly↑$^1$PheTrp↑$^2$IleIleGlyGly, and AlaAlaAlaPhe↑$^1$GlyGly↑$^2$IleIleGlyGly placed in pro-urokinase instead of the natural sequence ArgProArgPheLys↑IleIleGlyGly would be examples suitable for measurement of gelatinase A, stromelysin and angiotensin converting enzyme, respectively. These enzymes convert modified pro-urokinase by hydrolysing at position ↑$^1$ resulting in a still inactive intermediate. An enzyme like cathepsin C (dipeptidyldipeptidase) is subsequently used to convert this inactive intermediate into an active enzyme by hydrolysis at position ↑$^2$. Activity can thereafter be measured by any suitable procedure.

To introduce a new aminoacid sequence conferring a new desired specificity for activation to an existing proenzyme several methodologies can be followed. In many cases recombinant DNA technology appears an attractive option. A cDNA coding for the particular proenzyme must be available. Such a cDNA can be obtained using existing technology from a cDNA library e.g. by screening with specific oligonucleotides and cloning or alternatively with the aid of the polymerase chain reaction using two specific oligonucleotides flanking the coding sequence of the proenzyme. The coding sequence is introduced in a plasmid between a strong promoter and suitable termination sequences. Which promoter and termination sequences are selected depends on the expression system. For expression in mammalian cell lines such as chinese hamster ovary cells (CHO-cells), a cell line often employed for expression of recombinant proteins, a SV40 virus promoter and a beta globulin termination signal can be used, but many other strategies such as the use of insect cells may lead to comparable results.

Of particular interest could be expression of the mutated proenzyme in a micro-organism such as *E. coli* or yeast. Those expression systems are easy to handle, cheap and relatively simple to scale up to high production levels. Depending on the particular proenzyme a certain expression system is chosen since not all proenzymes can satisfactorily be expressed in all systems depending on the properties of the proenzyme such as presence of disulfide bonds, which are generally not formed in *E. coli,* but can in some cases be introduced later after expression. Furthermore, *E. coli* expressed proteins will not be glycosylated whereas yeast expressed proteins often are over-glycosylated. Whether glycosylation is of any importance for the proenzyme function cannot always be predicted, but it can easily be determined by some routine experimentation.

When an expression plasmid is constructed containing the natural wild-type coding sequence of the proenzyme, appropriate modifications are introduced into the DNA such that after expression a modified amino acid sequence around its activation site results. This new sequence is chosen such that it can be cut by the protease to be assayed. Introduction of new sequences into a cDNA can easily be reached by site-directed mutagenesis using mismatched synthetic oligonucleotides following standard protocols. Alternatively various adaptations of the polymerase chain reaction, always using one or more mismatched synthetic oligonucleotides can be employed. Another possible method of introducing mutations into cDNA is by partial or even complete vitro synthesis of the coding sequence. When the mutation has been introduced into the DNA its presence and the absence of secondary undesirable mutations can be verified by nucleotide sequencing using existing methodology. In all cases the modified cDNA is used to express a modified proenzyme. This proenzyme can be purified and concentrated using standard methodology. When applied in an assay kit additions might be required to stabilize the proenzyme during prolonged storage.

A convenient way to identify the optimal sequence in the activation region could be to make a random selection of all possible DNA sequences e.g. by using completely or partially randomized oligonucleotides for the introduction of mutations. When this random sequence library is expressed such that the expression product of single clones can be tested for its properties, an efficient optimization of the activation sequence can be reached. Using such procedures, thousands of different sequences could be screened.

The expression plasmid containing the (optimally) modified coding sequence for the proenzyme and appropriate regulatory and selection sequences (most conveniently sequences conferring resistance to certain antibiotics) is introduced into a suitable host organism. Using the selection sequences present, stable transformed cells are isolated by standard cloning techniques. These cloned cells are used to express the modified proenzyme. From the cells or the culture media the modified proenzyme is isolated and purified using existing methodology such as ion-exchange chromatography, gel filtration or affinity chromatography.

Recombinant DNA technology is not the only possible way to introduce the required modifications. Some especially smaller modifications can also be introduced by other e.g. chemical methods directly into the proenzyme.

Such a modified proenzyme can be part of a "kit" containing all necessary materials to perform a number of determinations. Typically, such a kit comprises containers with sufficient quantities of modified proenzyme, a suitable substrate to detect activated proenzyme, a suitable standard preparation to quantify the protease to be measured and materials to prepare buffer solutions. Furthermore, a kit might also contain specific antibodies to increase the specificity of the assay by specific quenching of the activity of a certain protease or specific binding of a protease, and one or more 96-well microtiter plates. It might be required to add stabilizers to the proenzyme to increase its stability during transport and storage. Such stabilizers could be other proteins like albumin, carbohydrates like mannitol, antioxidants or other organic chemicals. Furthermore inorganic salts might also have beneficial effects on stability. Most conveniently the proenzyme is present in lyophylized form and has to be reconstituted by buffer or water shortly before use. In addition, a description how to perform the determination and the calculation of the activity is included. Another possibility to increase the specificity is to employ a "BIA" procedure: first the protease to be measured is catched using a specific immobilized (monoclonal) antibody followed by measurement of the activity of the catched enzyme. Alternatively a kit or device might be of the "dipstick" type where all necessary reagents present in a dry form are immobilized on a strip or dot of material.

EXAMPLES

The following examples are just illustrations of the invention and by no means limit the applicability or scope of the invention.

Example I
Preparation of modified pro-urokinase

In this example the preparation of modified pro-urokinase as a substrate for metalloproteases, in particular matrix-metalloproteases such as for example collagenase is described.

Pro-urokinase is a single-chain proenzyme which can be activated by e.g. plasmin which hydrolyses the peptide bond between lysine-158 and isoleucine-159 resulting in the active two-chain form urokinase.

Figure 1:
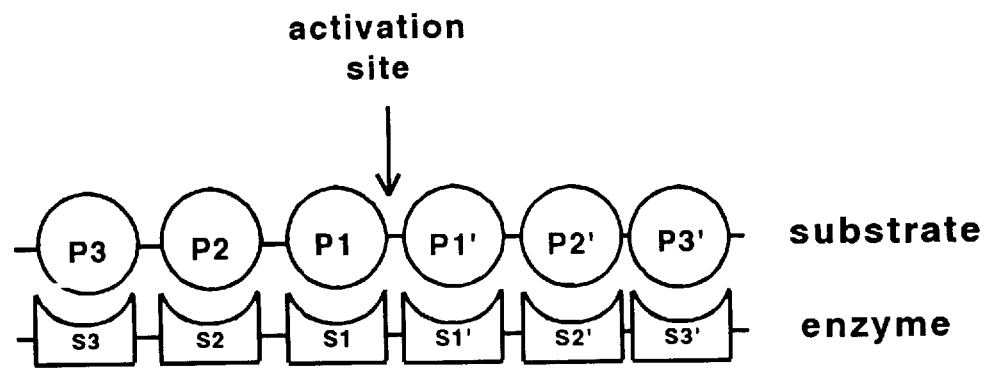
FIG. 1 schematically illustrates the concept of substrate recognition by proteases in general; the proteolytic enzyme responsible for activation of the substrate comprises aminoacid residues s3, s2, s1, s1', s2' and s3' which, in the example shown, are involved in recognition of the aminoacid residues P3, P2, P1, P1', P2' and P3' which form the activation site of the substrate; activation results in cleavage of the peptide bond between residues P1 and P1'.
Figure 2:
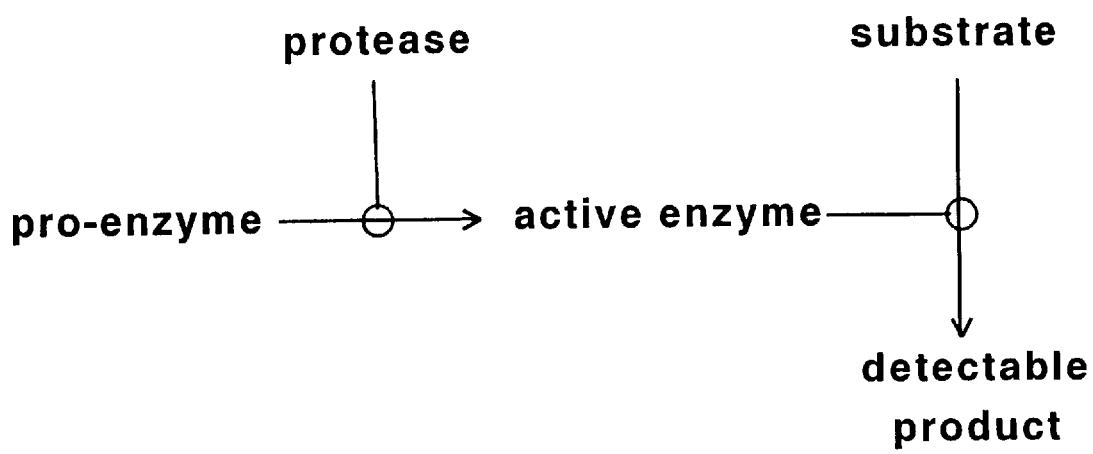
FIG. 2 schematically illustrates the principle of the coupled assay for protease measurement according to this invention; the protease to be detected can activate the modified pro-enzyme engineered to contain an activation site cleavable by said protease, and the active enzyme formed is detected by using a suitable substrate of said enzyme and observing or measuring a detectable product formed from the substrate.
Figure 3:
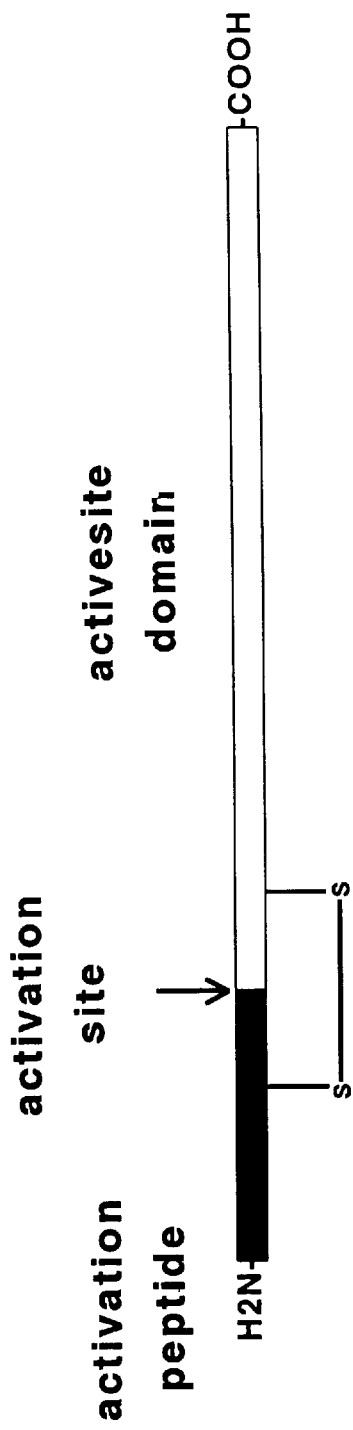
FIG. 3 schematically illustrates the concept of proenzyme activation by limited proteolysis; as shown, the proenzyme comprises an activation peptide at the N-terminal end which activation peptide may remain connected to the active site domain after activation (which involves cleavage of the peptide bond between residues P1 and P1' at the activation site) by, e.g., a disulfide bridge, but this is not necessarily so.
Figure 4:
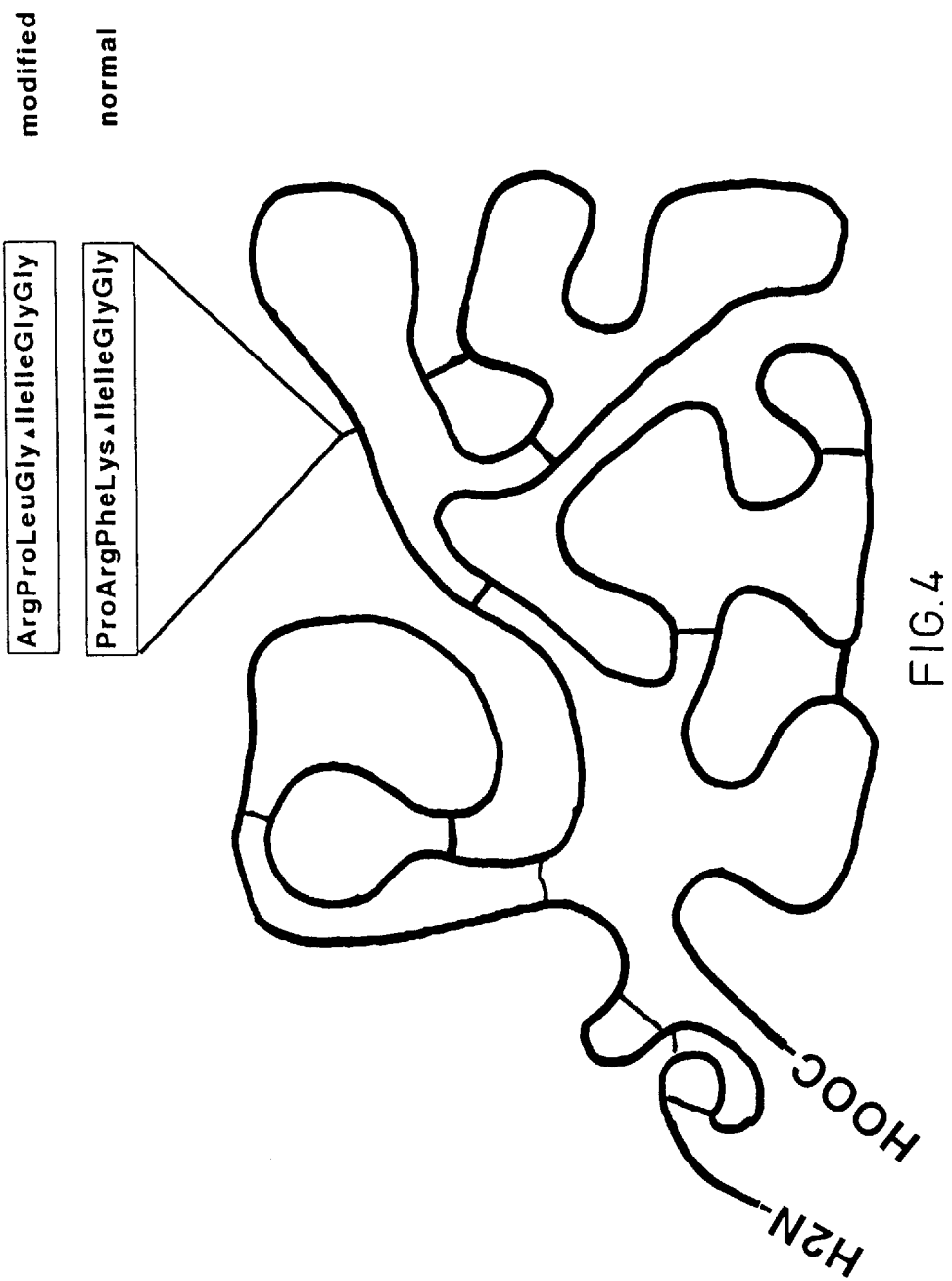
FIG. 4 schematically illustrates a modified pro-urokinase for detection of collagenases and other matrix metalloproteases; the pro-urokinase activation site comprising the aminoacid sequence ProArgPheLysIleIleGlyGly has been replaced by the aminoacid sequence ArgProLeuGlyIleIleGlyGly (SEQ ID NO: 1) which can be cleaved by collagenase and other matrix metalloproteases.

Upon comparison of the known amino acid sequences where collagenase cuts collagen or model substrates a consensus sequence was derived that is recognized by many different matrix-metalloproteases, including collagenases, gelatinases and stromelysins. Such a consensus sequence is starting from the N-terminal Pro-Leu-Gly ↑Ile-Xxx-Gly. For the various matrix-metalloproteases especially the Pro and both Gly residues appear to be important, the Leu and Ile residues are much less critical whereas residue Xxx might be almost any amino acid residue. When this consensus sequence was compared with the sequence around the activation site in normal wild-type pro-urokinase: -Pro-Arg-Phe-Lys ↑Ile-Ile-Gly-Gly-, it was decided to replace this sequence by -Arg- Pro-Leu-Gly ↑Ile-Ile-Gly-Gly wherein the matrix-metalloprotease consensus sequence is indicated by the box and the arrow indicates the desired place of hydrolysis. It must be noted that this sequence is just one of the many possibilities used to illustrate the invention (FIG. 4).

a. Isolation of cDNA coding for human urokinase.

The complete protein coding region of the u-PA cDNA was isolated from poly A+ mRNA from the u-PA producing fibrosarcoma cell line HT1080 (Quax et al. (1990) Cancer Res. 50, 1488–1494) using Reverse Transcriptase-Polymerase Chain Reaction technique. The following oligonucleotides: TAGCGCCCCGGGCTCGCCACCAT (SEQ ID NO: 2) and ACGGGTCTGGGGAGACCGGT (SEQ ID NO: 3), were used as primers to amplify a cDNA fragment spanning nucleotide 99 to 1620 in human u-PA cDNA.

b. Construction of expression vector for urokinase.

This fragment was cloned into the eukaryotic expression plasmid pEV2tPA (De Munk et al. (1989) Biochemistry 28, 7318–7325; Verheijen et al. (1986) EMBO J 5, 3525–3530) by replacing the t-PA cDNA fragment. To accomplish this, pEV2tPA was digested with BglII and the u-PA cDNA fragment was cloned into the pEV2 vector using the following specific linker oligonucleotides:

AGCTTCCCGGGAGGCCTGTCGACA (SEQ ID NO: 4) and

GATCTGTCGACAGGCCTCCCGGGA (SEQ ID NO: 5).

c. Introduction of mutations in urokinase expression vector.

Mutations in the urokinase expression vector peV2uPA1.1 were introduced using the recombinant circle polymerase chain reaction method. The following four different oligonucleotides were synthesized:

UKCOL1A: cggcggctcgggattattgggggagaattcacc (SEQ ID NO: 6)

UKCOL2A: cccgagcggccgcctcagagtcttttggccaca (SEQ ID NO: 7)

UKCOL3A: attattgggggagaattcacc (SEQ ID NO: 8)

UKCOL4A: cctcagagtcttttggccaca (SEQ ID NO: 9)

Two independent polymerase chain reactions (PCR) were performed. Oligo UKCOL1A was combined with UKCOL4A, and UKCOL2A with UKCOL3A.

PCR were performed in a total volume of 100 microliter containing 2 nanogram plasmid DNA peV2UK1.1, 1 micromolar of each of the two oligonucleotides, 0.2 millimolar of all four deoxyribonucleotides, 5 units of Taq DNA polymerase and an appropriate buffer as supplied with the polymerase, finally the contents of the tubes were covered with oil. Twenty to thirty cycles of PCR with the following temperatures were performed: 1 min 94° C., 1 min 55° C. and 3 min 72° C. Both PCR products were electrophoresed on low melting agarose gels, cut from the gel and isolated by electroelution followed by ethanol precipitation.

The two PCR products obtained with the primer combinations UKCOL1A/UKCOL4A and UKCOL2A/

UKCOL3A were mixed in equimolar quantities, denatured for 5 min at 100° C. and reannealed by cooling in 10 min intervals at temperatures decreasing in 10° C. steps to 55° C. in 10 mM Tris-HCl, 1 mM EDTA, 100 mM NaCl, pH 8.0. A small quantity of this reannealed material was used to transform E. coli JM109 following an established protocol (Molecular Cloning: A Laboratory Manual, 2nd ed. Sambrook, Fritsch & Maniatis, eds. CSH 1989). After overnight incubation at 37° C. colonies appeared which were picked, grown in small cultures and used for isolation of plasmid DNA according to standard procedures. Plasmid DNAs were cut with the restriction enzymes AvaI or DraII. The first enzyme will not cut the wild-type plasmid but will cut the mutant plasmid at one position. DraII cuts the wild-type plasmid four times whereas the mutant plasmid will be cut only three times. With this procedure several potential mutant clones were selected and large scale plasmid preparations were made. The presence of the desired mutation and the absence of other mutations was verified by DNA sequencing using the dideoxy chain termination methods.

d. Expression of mutant pro-urokinase.

Ten to twenty $\mu$g of the expression plasmid peV2UKcol was transfected into Chinese hamster ovary cells together with 2 $\mu$g of pSV2neo plasmid containing a selectable marker. Transfection was performed using the calcium-phosphate co-precipitation method. To the culture medium 1 mg/ml of the neomycin analog G418 was added and resistant clones, appearing after 2–3 weeks of culture were selected. Selected clones were grown separately and 24 h conditioned medium was collected. Production of pro-urokinase mutant was verified by an enzyme immunoassay using a published procedure (Binnema et al. (1986) Thromb. Res. 43, 569–577). High producing clones were expanded and grown in roller bottles in serum-free medium. Medium was collected, centrifuged and stored at −20° C.

After thawing pro-urokinase mutant was adsorbed from the medium to zinc chelate sepharose. After extensive washing mutant pro-urokinase was eluted with 50 ml imidazole. Alternatively medium was adsorbed to a column of immobilized monoclonal antibody to urokinase in tandem with a Sephadex G25 column. After extensive washing mutant pro-urokinase was eluted with 3 molar KSCN and subsequently dialysed against a suitable buffer.

Example II
Characterization of modified pro-urokinase

The mutant pro-urokinase purified as described above was analyzed by polyacrylamide gel electrophoresis in the presence of sodium dodecylsulphate after visualization by silver staining. One major band at the expected molecular weight of 55 kDa was observed and surprisingly little contaminants, even after the single-step purification procedure of example I.

Figure 5:
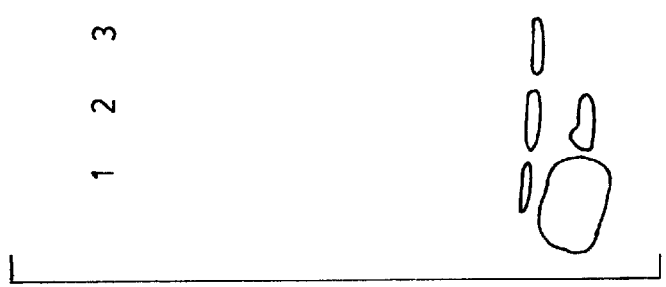
FIG. 5 shows in lane 3 the results of SDS-PAGE and fibrin zymography of the purified mutant pro-urokinase; lane 1: pro-urokinase incubated with collagenase; lane 2: EDTA, an inhibitor of collagenase. A drawing of said results is shown.

Use of a zymographic technique after gel electrophoresis (Granelli-Piperno et al. (1978) J. Exp. Med. 148, 223–234) revealed that the material had hardly any proteolytic activity as expected for a pro-urokinase preparation (FIG. 5). The absence of activity was confirmed by incubation with the substrate L-pyroGlu-Gly-Arg-p-nitroanilide, a specific chromogenic substrate for urokinase. Incubation of mutant pro-urokinase with plasmin did not increase its activity unlike that of wild-type pro-urokinase. When mutant pro-urokinase was incubated with collagenase the activity increased, whereas EDTA, an inhibitor for collagenase, inhibited activation (FIG. 5).

In another experiment, mutant pro-urokinase was incubated with collagenase for various time periods and at various concentrations. Samples were taken and used for electrophoretic analysis under reducing conditions, followed by western blotting, incubated with rabbit anti-urokinase antibodies, peroxidase-labelled goat anti-rabbit IgGs and visualized with a chemiluminescence kit (Boehringer Mannheim GmbH).

Figure 6:
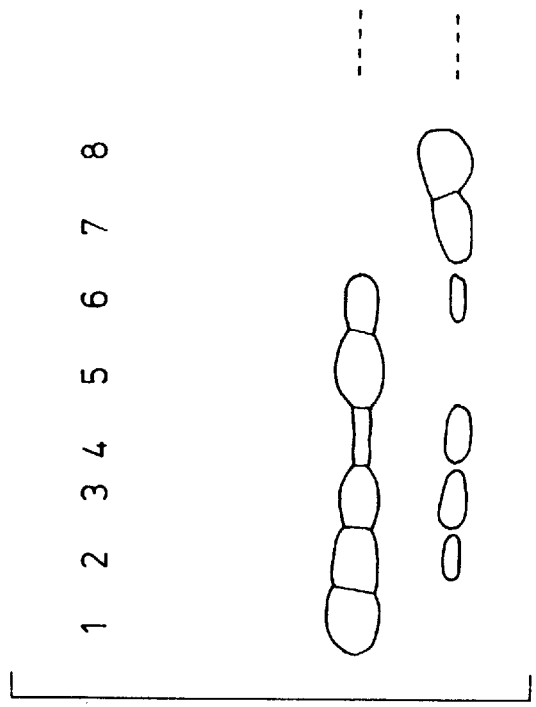
FIG. 6 shows the results of a Western blot to visualize mutant urokinase (32 ng) after incubation with collagenase for various time points and various concentrations (t=0–6 h). Lanes 1–5: 15 ng collagenase; lane 6: 7.5 ng collagenase; lane 7: 30 ng collagenase. A drawing of said results is shown.

Furthermore, aliquots of the same material were used for activity measurements using L-pyroGlu-Gly-Arg paranitroanilide. It is shown in FIG. 6 that incubation with collagenase results in a decrease of the band at 55 kDa and a parallel increase in a band of about 30 kDa, as expected when collagenase would cut the new sequence N-terminally of residue 159 (FIG. 4). Conversion of single-chain 55 kDa pro-urokinase into the low molecular weight products is accompanied by an increase in activity as measured with chromogenic substrate (Table 4). Conversion and activation can be inhibited by EDTA, an inhibitor of collagenase. Incubation of mutant pro-urokinase with plasmin has no effect.

These results indicate that mutant pro-urokinase might be a suitable substrate for determination of collagenase.

TABLE 4

Activity measurement of mutant pro-urokinase (32 ng) with collagenase, for different time points and different concentrations, using plasminogen and a chromogenic plasmin substrate

| collagenase (ng) | time (h) | activity ($\Delta A/h^2 * 1000$) |
| --- | --- | --- |
| 15 | 0 | 0 |
| 15 | 1 | 111 |
| 15 | 2 | 178 |
| 15 | 6 | 343 |
| 15 + EDTA | 6 | 3.8 |
| 7.5 | 6 | 197 |
| 30 | 6 | 361 |

Example III
Determination of collagenase activity using mutant pro-urokinase

Several methods for determination of collagenase using mutant pro-urokinase were investigated.

a. Method I.

Figure 7:
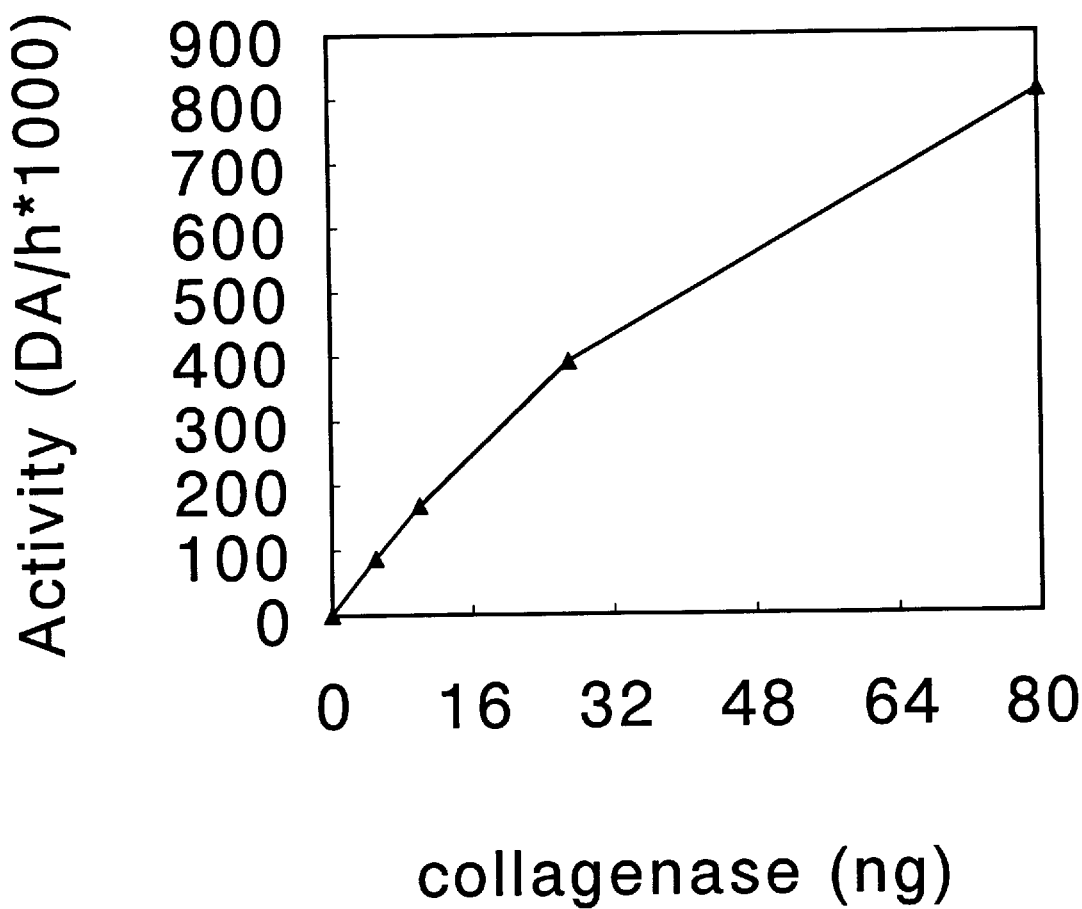
FIG. 7 shows the activity as a function of the amount of collagenase. Mutant pro-urokinase (252 ng) was incubated at 37° C. with various amounts of collagenase. After 6 hours EDTA was added +pyro-Glu-Gly-Arg-pNA (0.4 mM). The absorbance change at 405 nm and 25° C. was measured.

Collagenase at various concentrations was incubated with mutant pro-urokinase at 37° C. in 0.1 mol/l Tris-HCl buffer of pH 7.5 after various incubation times. Samples of 50 microliter were taken and mixed with 10 microliter of 0.5 M EDTA, to stop the collagenase catalyzed conversion of mutant pro-urokinase to active mutant urokinase. Subsequently mutant urokinase activity was measured by incubation with 0.4 mM pyro-Glu-Gly-Arg-pNA at 25° C. in 0.1 mol/l Tris-HCl buffer pH 7.5 in a total volume of 250 microliter. The incubations are preferably conducted in 96-well flat-bottom microtiter plates, enabling rapid measurement of absorbance change in suitable reading equipment. The results of such an experiment are shown in FIG. 7.

Alternatively both reactions, the collagenase-catalyzed conversion of pro-urokinase and the urokinase-catalyzed hydrolysis of pyro-Glu-Gly-Arg-paranitroanilide, can be performed in the same reaction vessel leading to a parabolic rate assay. In this case no EDTA is added. This latter option minimizes the number of liquid handling steps, but does not allow to optimize reaction conditions for collagenase catalyzed modified pro-urokinase activation and tripeptide-substrate hydrolysis separately.

b. Method II.

Figure 8:
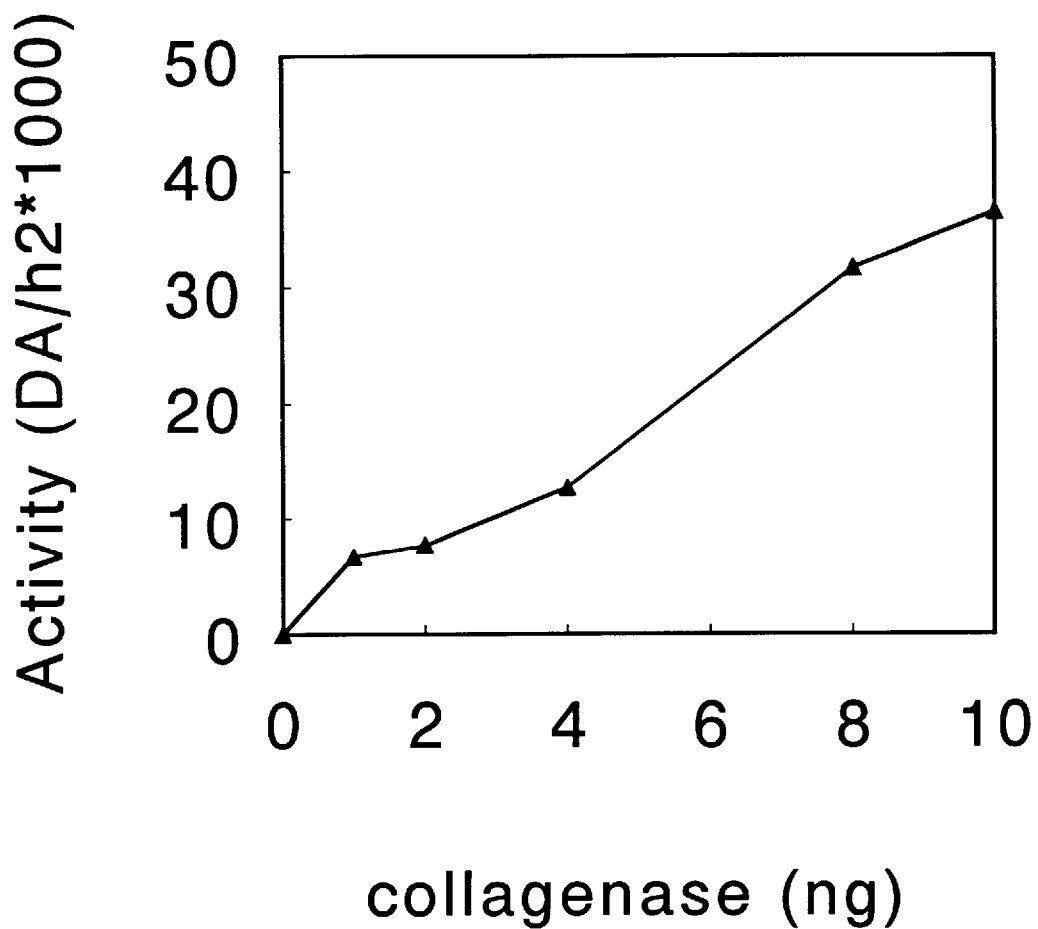
FIG. 8 shows the results obtained in a single-step activity measurement with plasminogen and H-D-Val-Leu-Lys-pNA.

As described for method I collagenase is incubated with mutant pro-urokinase and after defined incubation periods the reaction is stopped by addition of EDTA. Subsequent measurement of urokinase activity employs plasminogen and a chromogenic plasmin substrate (FIG. 8). Examples of suitable plasmin substrates can be found in Table 5. This assay is considerably more sensitive than the assay of method I due to an extra amplification step.

TABLE 5

Examples of suitable plasmin substrates

Figure 9:
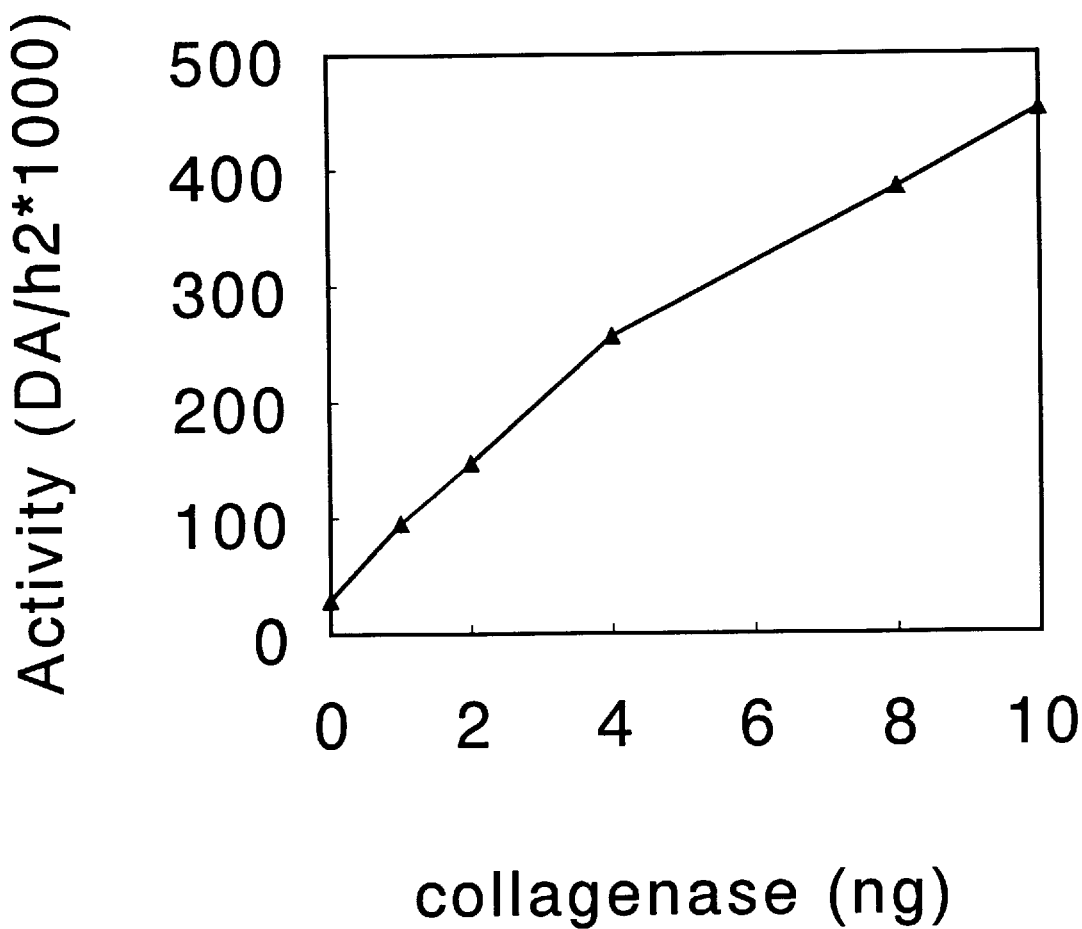
FIG. 9 shows the results obtained in a two-step activity measurement with plasminogen and H-D-Val-Leu-Lys-pNA.

H-D-Val-Leu-Lys-pNA
N-isovaleryl-Leu-Lys-pNA
N-isovaleryl-Phe-Lys-pNA
N-acetyl-D-Val-Phe-Lys-pNA
N-acetyl-D-Val-Leu-Lys-pNA
ε-aminocaproyl-D-Val-Leu-Lys-pNA
N-O-sulphobenzoyl-Val-Leu-Lys-pNA
N-carbobenzoxy-Val-Leu-Lys-pNA Alternatively also this assay can be performed in a single step with some advantages and disadvantages as mentioned above (FIG. 9). In this case three coupled reactions are involved, a collagenase-catalyzed conversion of mutant-pro-u-PA to mutant-u-PA, a mutant-u-PA-catalyzed conversion of plasminogen into plasmin and a plasmin-catalyzed conversion of a peptide substrate.

c. Method III.

The above described methods are very suitable for quantification of collagenase-like enzymes. In both methods I and II the reactions are performed in solution. When mixtures of collagenase-like enzymes are present such methods are of limited use. In such cases zymographic methods detecting enzyme activity after gelelectrophoretic separation are attractive options. In the method described here, the presence of collagenase-like enzymes can be visualized after separation by polyacrylamide gel electrophoresis in the absence or presence of sodium dodecylsulphate. Collagenase-containing samples are separated by electrophoresis on a polyacrylamide separating gel in the presence of sodium dodecylsulphate. After electrophoresis the gel is washed three times 20 min in 1% (v/v) Triton X-100™ to renature the enzymes. A detection gel is prepared by mixing plasminogen, fibrinogen, mutated pro-urokinase and molten agarose 25% (w/v) in 50 mM Veronal HCl, pH 7.75 containing 0.65 mM $CaCl_2$, 0.65 mM $MgCl_2$ and 140 mM NaCl. The agarose solution must be cooled to around 42° C. before the other components are added. Subsequently thrombin is added and the solution is rapidly mixed and poured in a clean flat-bottomed glass or plastic container. After solidification the washed polyacrylamide gel is placed on the agarose layer. The sandwich is incubated at 25°–37° C. for several hours in a humidified chamber. The presence of active collagenase is shown by clear lysis zones in an opaque background of fibrin (FIG. 5).

d. Method IV.

Figure 10:
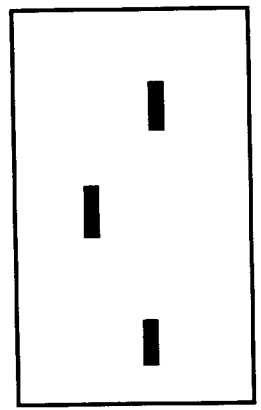
FIG. 10 schematically illustrates a method for detecting a matrix metalloprotease (MMP) after blotting on a filter using plasminogen (PLG) as a substrate for urokinase which is the active enzyme formed from the modified pro-urokinase used as the proenzyme. The plasmin (PLM) formed as a result of hydrolysis of the plasminogen is detected by using a chromogenic plasmin substrate which is converted by plasmin into a detectable product.
Figure 10:
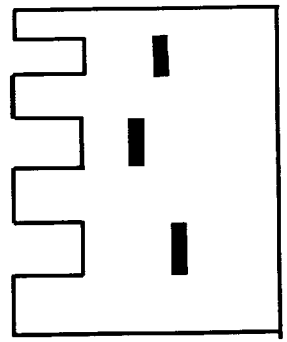
Figure 10:
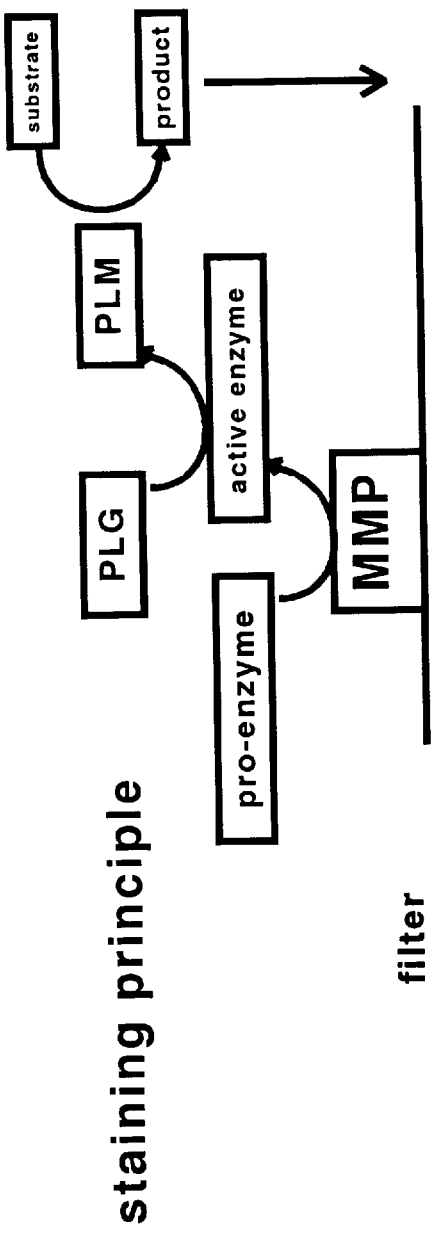

As an alternative for detection of collagenases in polyacrylamide gels, proteins can be transferred to e.g. nitrocellulose or nylon sheets by e.g. electro-blotting. Blots are blocked with a suitable protein like albumin or casein and activity is visualized by incubation with mutated pro-urokinase, plasminogen and chromogenic plasmin substrate in a suitable buffer like Tris-HCl of pH 6–8 (the principle is illustrated in FIG. 10). After incubation at 25°–37° C. for 30 min to several hours, the blot is incubated in 0.1 mol/l HCl containing 0.1% (v/v) $NaNO_2$ immediately followed by an incubation for 5 min in 0.1 ml/l HCl containing 0.5% (w/v) $(NH_4)_2SO_4$. Finally the blot is transferred to 0.05% (w/v) N-1 naphthylethylenediamine solution in 47.5% (w/v) ethanol for about 3 min until a red colour emerges.

The procedure can also be performed by placing the blot on a thin agarose layer containing modified pro-urokinase, plasminogen and a chromogenic plasmin substrate. Compared with incubation in solution sharper bands are obtained and less material is consumed.

An analogous procedure can be used to stain enzyme activity on tissue sections.

Example IV

Determination of matrix-metalloproteases

Human mmp-2 and mmp-9 were isolated from conditioned medium of human umbilical vein endothelial cells using gelatine-sepharose™ affinity chromatography. The purified material is largely inactive and can be activated by treatment with aminophenyl mercuric acetate. An aliquot containing either activated or non-activated mmp-2 and mmp-9 was incubated with 0.15 μM modified pro-urokinase at 37° C. in 0.1 mol/l Tris-HCl, pH 7.5, 0.01% v/v Tween-80™ for a period between 0–48 h. In control experiments a mmp-mixture plus 5 mM EDTA or no mmp-mixture was added. After incubation EDTA was added to a final concentration of 5 mM and aliquots were mixed with plasminogen (0.15 μM final concentration) and a plasmin substrate such as H-D-Val-Leu-Lys-para-nitroanilide in a suitable buffer like 0.1 mol/l Tris-HCl with pH 7.5 containing 0.01% v/v Tween-80™. These mixtures were incubated at 25° or 37° C. and the absorbance change at 405 nm was measured at regular intervals. The results of such an experiment are summarized in Table 6.

TABLE 6

Activity measurement of mutant pro-urokinase with a mixture of MMP2 and MMP9, inactive and activated with APMA, at different time points. Measured with plasminogen and a chromogenic substrate of plasminogen

| time (h) | activated MMP ($\Delta A/h^2 * 1000$) | not activated MMP ($\Delta A/h^2 * 1000$) |
| --- | --- | --- |
| 0 | <0.05 | <0.05 |
| 1 | 0.3 | <0.05 |
| 2 | <0.05 | <0.05 |
| 3 | <0.05 | <0.05 |
| 4 | 1.1 | <0.05 |
| 6.5 | 1.3 | <0.05 |
| 24 | 3.6 | 1.0 |
| 31 | 35.9 | 2.1 |
| 48 | 48.9 | 14.0 |
| 48 + EDTA | <0.05 | <0.05 |

Example V

Kit for determination of protease activity

Such a kit preferably comprises: containers with measured amounts of modified proenzyme, frozen or preferably stabilized by e.g. lyophylization in the presence of carbohydrates or other proteins, containers with a suitable substrate for the active enzyme, a container containing a stabilized control preparation and containers with concentrated or lyophilized buffer preparations and when required one or more specific antibody or inhibitor preparations to increase specificity. Furthermore the kit might contain one or more 96-well microtiter plates and a description how to perform the determination and calculate the results.

Example VI

Comparison of response with various purified matrix-metalloproteases

Equal molar quantities (10 nM final concentration) of activated human matrix-metalloproteases were incubated with 750 ng (final concentration 50 nM) of modified pro-urokinase and 0.6 mM of the urokinase substrate pyro-Glu-Gly-Arg-pNA in 50 mM Tris.HCl pH 7.6, 150 mM NaCl, 5 mM CaCl$_2$, 1 μM ZnCl$_2$ and 0.01% (v/v) BRIJ-35™ at 37° C. in a total volume of 0.25 ml. The absorbance change was followed in time (0–4 hours) and the reaction rate expressed as $\Delta A/h^2$. Reactions were performed in the absence (hatched bars) and presence (solid bars) of 1 mM EDTA.

Figure 11:
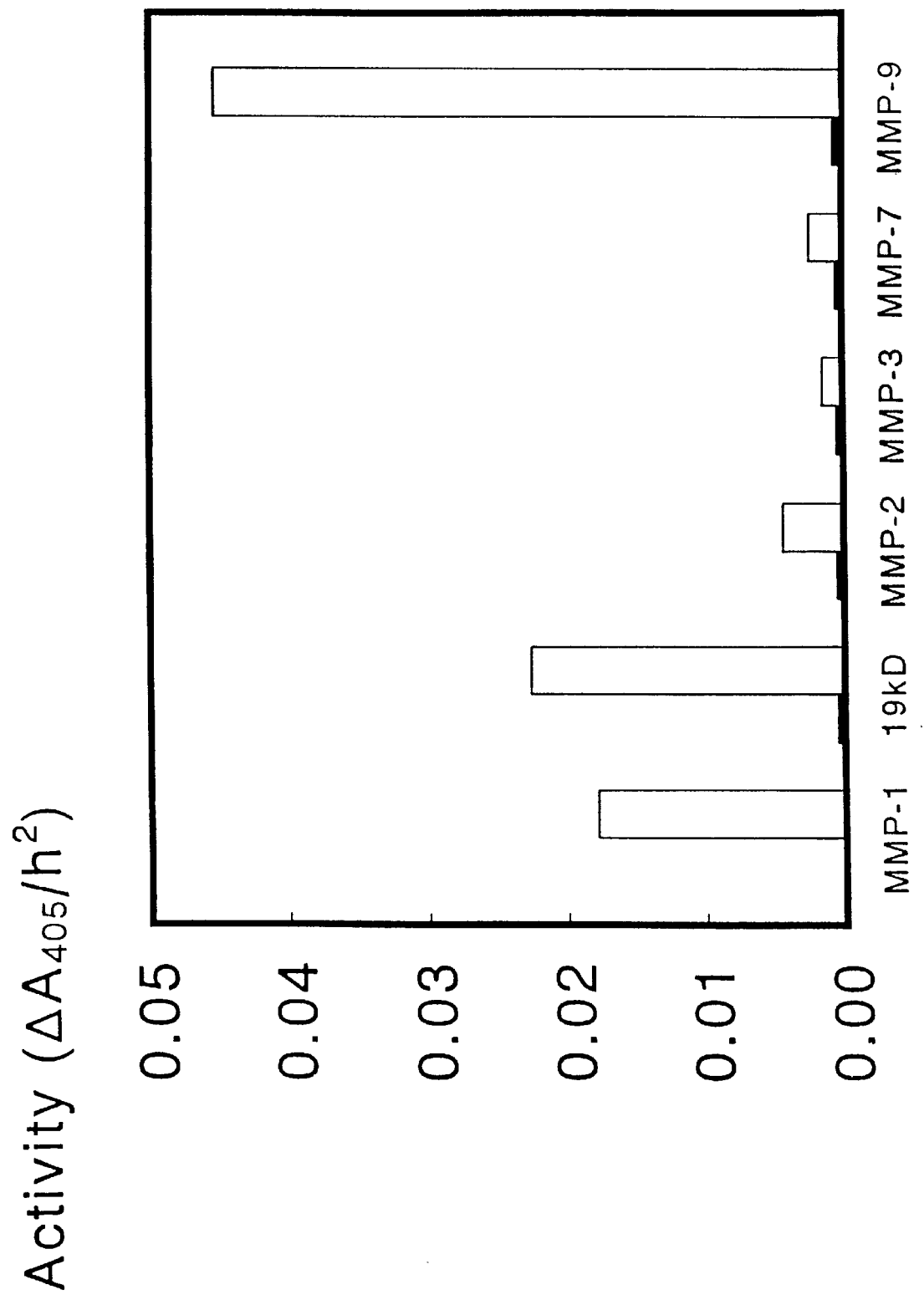
FIG. 11 shows the activity, expressed as $\Delta A/h^2$, obtained by contacting modified pro-urokinase and the urokinase substrate pyro-Glu-Gly-Arg-pNA in the absence (hatched bars) or presence (solid bars) of 1 mM EDTA with various activated human matrix-metalloproteases.

The results (FIG. 11) show that no activity is detected in the presence of EDTA indicating the specificity for matrix-metalloproteases. The assay is most sensitive for MMP-1 and MMR-9. The high sensitivity for MMP-1 is remarkable since this enzyme generally has a low activity on non-collagen substrates.

Example VII
Parabolic rate assay for human MMP-9

Activated human MMP-9 (250 pM final concentration) was incubated at 37° C. with 750 ng of modified pro-urokinase and 0.6 mM pyro-Glu-Gly-Arg-pNA in the presence (triangles) and absence (circles and diamonds, duplicate experiment) of 1 mM EDTA. During a 7 hours incubation at 37° C. in a buffer as described in Example VI, the absorbance change was followed.

Figure 12:
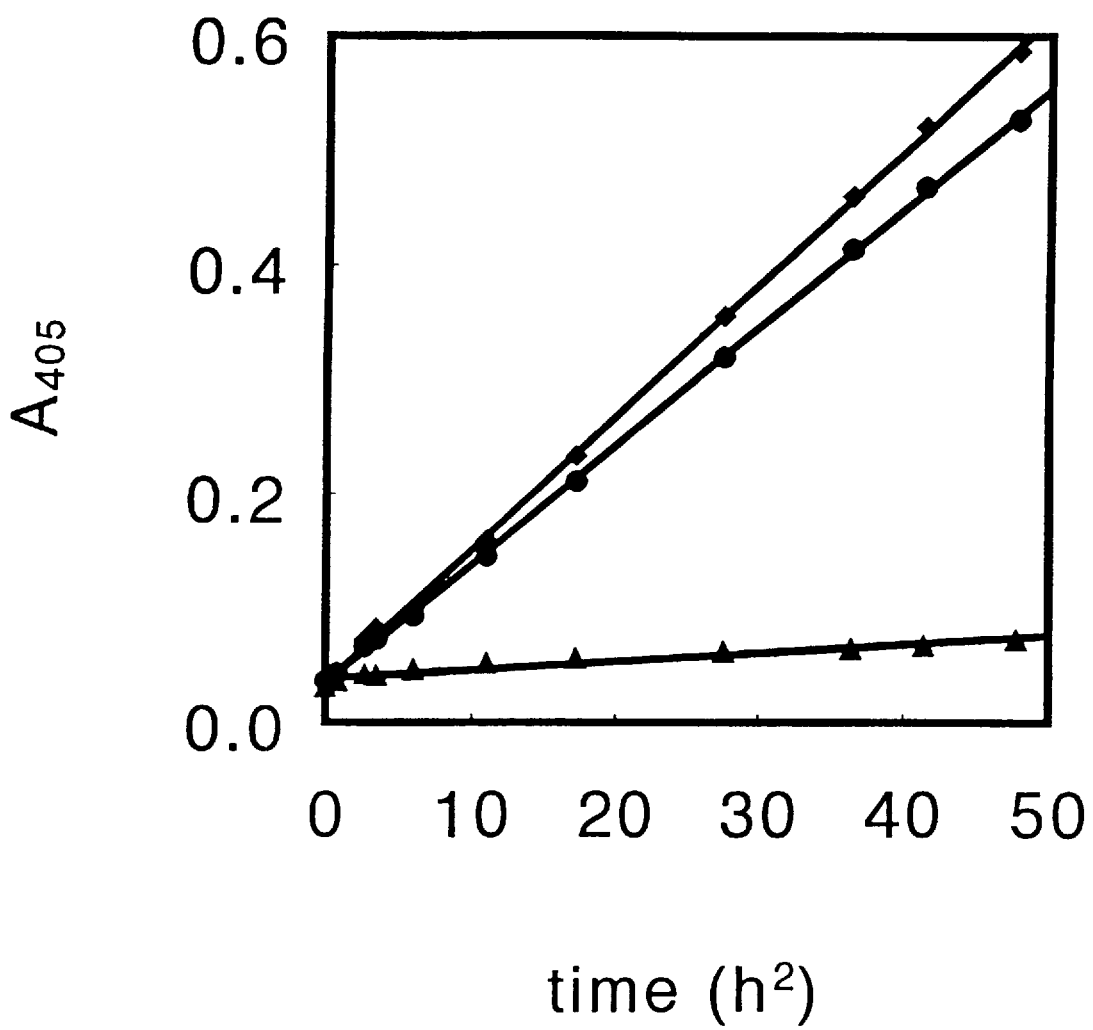
FIG. 12 shows the absorbance at 405 nm as a function of time, obtained by incubating modified pro-urokinase and pyro-Glu-Gly-Arg-pNA with activated human MMP-9 in the presence (triangles) or absence (circles and diamonds, duplicate experiment) of 1 mM EDTA.

The absorbance change in the absence of EDTA was found to be linear with the square of the incubation duration. In the presence of EDTA hardly any activity was found (FIG. 12).

Example VIII
Determination of detection limit for MMP-9

Activated human MMP-9 of 0–500 pM final concentration, corresponding with 0–125×10–15 mol of enzyme per incubation, was incubated with modified pro-urokinase and pyro-Glu-Gly-Arg-pNA with and without 1 mM EDTA as described in Examples VI and VII. The absorbance change was monitored after various time intervals between 0 and 7 hours. The activity was expressed as $\Delta A/h^2$.

Figure 13:
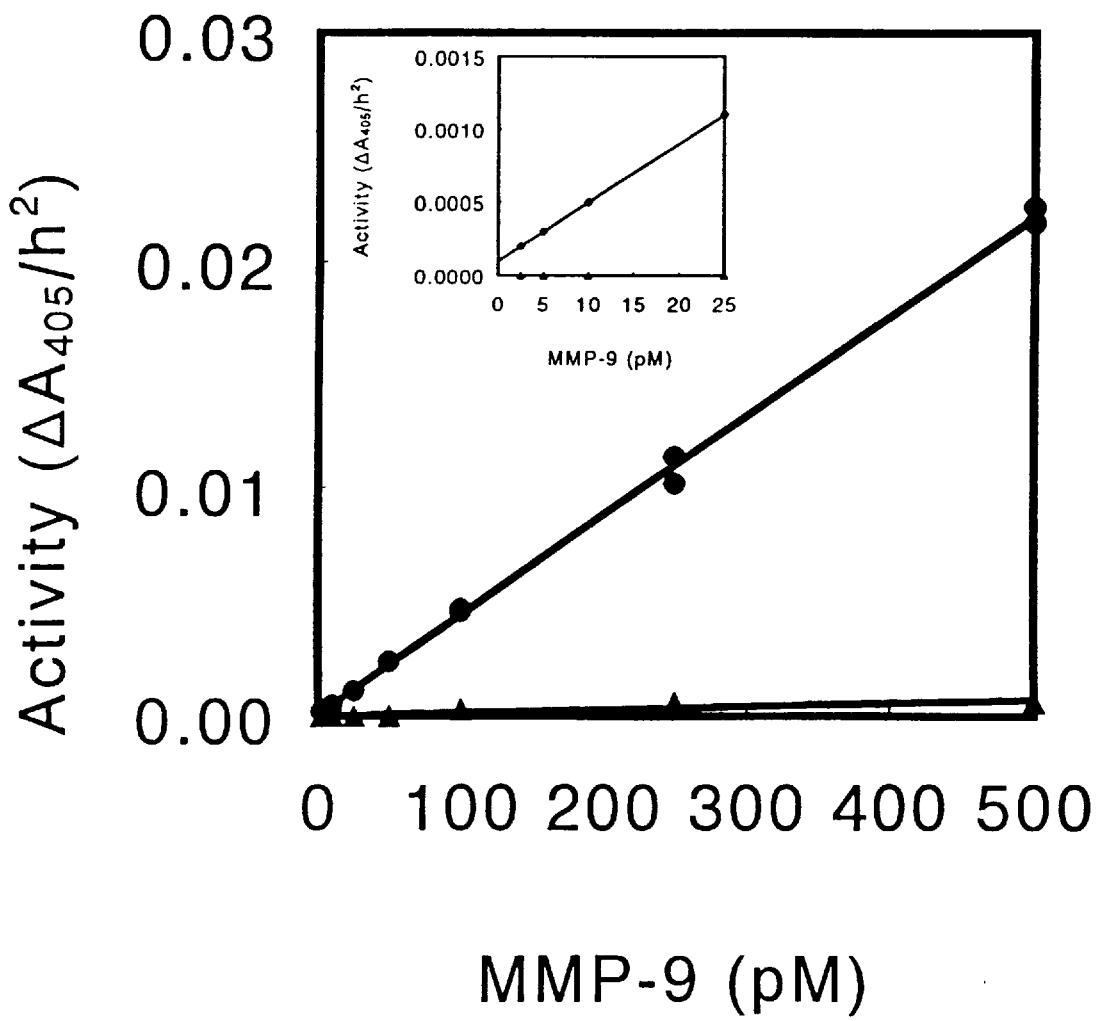
FIG. 13 shows the activity, expressed as $\Delta A/h^2$, obtained by contacting modified pro-urokinase and pyro-Glu-Gly-Arg-pNA in the absence (circles) or presence (triangles) of 1 mM EDTA with various final concentrations (from 0 to 500 pM) of activated human MMP-9.

The inset shows the part of the graph with MMP-9 concentrations of 0–25 pM. Even at concentrations below 5 pM of MMP-9 a reliable response, linear with the concentration can be obtained (FIG. 13).

Example IX

Determination of MMP activity in biological samples

Using the procedure of Example VII, MMP activity was determined in a variety of biological samples. Each sample was measured with and without activation with amino-phenyl mercuric acetate (24 hours at 37° C.) and in the presence or absence of 1 mM EDTA. Total MMP activity is the activity measured with activation and without EDTA, active MMP activity is measured without activation and without EDTA. Activity in the presence of EDTA (very low) is subtracted.

Table 7 shows the results of these experiments. In several tissue extracts and biological fluids, the MMP activity can be determined.

TABLE 7

Measurement of pro-MMP and total MMP in various biological samples

| Sample | pro-MMP ΔA | total MMP ΔA |
|---|---|---|
| synovial tissue extracts | | |
| osteoarthritis | 0.012 | 0.052 |
| rheumatoid arthritis | 0 | 0.065 |
| synovial fluid | | |
| osteoarthrosis | 0.663 | 0.738 |
| rheumatoid arthritis | 2.650 | 2.654 |
| normal control | 0.012 | 0.014 |
| stomach tissue extracts | | |
| (mean of 4 patients) | | |
| normal | 0.016 | 0.030 |
| tumor | 0.712 | 0.756 |

I claim:

1. A method of determining a protease, or its precursor after activation, in a sample, comprising incubating the sample with a substrate of said protease, determining proteolytic cleavage of said substrate, and correlating data obtained therefrom in order to determine the protease, wherein said substrate is a modified proenzyme containing a recognition site which is cleavable by said protease.

2. The method as claimed in claim 1 wherein proteolytic cleavage of said modified proenzyme activates the proenzyme and is determined by observing or measuring the resulting activity using a suitable substrate of the activated proenzyme.

3. The method as claimed in claim 1 wherein proteolytic cleavage of said modified proenzyme converts it into a substrate for a secondary enzyme capable of activating the proenzyme, and said proteolytic cleavage of the modified proenzyme is determined by incubating with said secondary enzyme and observing or measuring the resulting activity using a suitable substrate of the activated proenzyme.

4. The method as claimed in claim 1 wherein said sample is selected from the group consisting of a biological fluid, a fraction of a biological fluid, a biological tissue, an extract of a biological tissue, and a fraction of an extract of a biological tissue.

5. The method as claimed in claim 1 wherein said protease is selected from the group consisting of serine proteases, cysteine proteases, aspartic proteases and metalloproteases.

6. The method as claimed in claim 1 wherein said protease is an aspartic protease or a metalloprotease.

7. The method as claimed in claim 1 wherein said protease is a matrix metalloprotease.

8. The method as claimed in claim 7 wherein said matrix metalloprotease is a collagenase, gelatinase or stromelysin.

9. The method as claimed in claim 1 wherein said modified pro-enzyme is derived from a proenzyme by replacing its activation site by an activation site which is cleavable by the protease to be determined.

10. The method as claimed in claim 1 wherein said modified pro-enzyme is derived from a serine esterase.

11. The method as claimed in claim 1 wherein said modified pro-enzyme is derived from a pro-phospholipase.

12. The method as claimed in claim 1 wherein said modified pro-enzyme is derived from a serine protease.

13. The method as claimed in claim 1 wherein said modified pro-enzyme is derived from a clotting enzyme selected from the group consisting of factor V, factor VII, factor IX, factor X, factor XII and prothrombin.

14. The method as claimed in claim 1 wherein said modified pro-enzyme is derived from a proenzyme selected from the group consisting of trypsinogen, chymotrypsinogen, plasminogen, pro-urokinase, pro-elastase, prosubtilisin and kallikrein.

15. The method as claimed in claim 1 wherein said modified pro-enzyme is derived from pro-urokinase.

16. The method as claimed in claim 15 wherein the pro-urokinase modification is in the region $Gly^{149}$ to $Glu^{168}$.

17. The method as claimed in claim 15 wherein the pro-urokinase modification is in the sequence $Pro^{155}$-Arg-Phe-Lys-Ile-Ile-Gly-$Gly^{162}$.

18. The method as claimed in claim 15 wherein the sequence $Pro^{155}$-Arg-Phe-Lys-Ile-Ile-Gly-$Gly^{162}$ is replaced by the sequence $Xxx^{155}$-Pro-Leu-Gly-Ile-Ile-Gly-$Yyy^{162}$, wherein Xxx and Yyy can be any aminoacid, to transform the pro-urokinase into a substrate for collagenase and other matrix metalloproteases.

19. The method as claimed in claim 15 wherein the sequence $Pro^{155}$-Arg-Phe-Lys-Ile-Ile-Gly-$Gly^{162}$ is replaced by the sequence $Arg^{155}$-Pro-Leu-Gly-Ile-Ile-Gly-$Gly^{162}$ to transform pro-urokinase into a substrate for collagenase and other matrix metalloproteases.

20. The method as claimed in claim 15 wherein activation of said modified pro-urokinase is determined using a peptide substrate of urokinase which releases a coloured or fluorescent group upon hydrolysis by urokinase.

21. The method as claimed in claim 15 wherein said peptide substrate is a compound Xxx-Yyy-Arg-pNA, wherein Xxx and Yyy can be any aminoacid and pNA represents a para-nitroaniline moiety.

22. The method as claimed in claim 15 wherein activation of said modified pro-urokinase is determined using plasminogen as urokinase substrate and using a plasmin-specific peptide substrate releasing a coloured or fluorescent group upon hydrolysis by plasmin to determine activation of said plasminogen.

23. The method as claimed in claim 22 wherein said plasmin-specific peptide substrate is selected from the group consisting of H-D-Val-Leu-Lys-pNA, N-isovaleryl-Leu-Lys-pNA, N-isovaleryl-Phe-Lys-pNA, N-acetyl-D-Val-Phe-Lys-pNA, N-acetyl-D-Val-Leu-Lys-pNA, ε-aminocaproyl-D-Val-Leu-Lys-pNA, N-O-sulphobenzoyl-Val-Leu-Lys-pNA and N-carbobenzoxy-Val-Leu-Lys-pNA.

24. A modified proenzyme derived from a proenzyme by providing it with a recognition site which is cleavable by a protease different from the one which activates the unmodified proenzyme.

25. The modified proenzyme as claimed in claim 24 wherein said recognition site is an activation site cleavable by a protease different from the one which activates the unmodified proenzyme, said activation site replacing the activation site of the proenzyme.

26. The modified proenzyme as claimed in claim 24 which is derived from pro-urokinase.

27. The modified proenzyme as claimed in claim 26 wherein the sequence $Pro^{155}$-Arg-Phe-Lys-Ile-Ile-Gly-$Gly^{162}$ is replaced by the sequence $Xxx^{155}$-Pro-Leu-Gly-Ile-Ile-Gly-$Yyy^{162}$, wherein Xxx and Yyy can be any aminoacid, to transform the pro-urokinase into a substrate for collagenase and other matrix metalloproteases.

28. The modified proenzyme as claimed in claim 26 wherein the sequence $Pro^{155}$-Arg-Phe-Lys-Ile-Ile-Gly-$Gly^{162}$ is replaced by the sequence $Arg^{155}$-Pro-Leu-Gly-Ile-Ile-Gly-$Gly^{162}$ to transform the pro-urokinase into a substrate for collagenase and other matrix metalloproteases.

29. A kit for determining a protease, or its precursor after activation, in a sample, comprising a modified proenzyme as defined in claim 24, together with at least one member from the group consisting of substrates for activated proenzyme, secondary enzymes, buffer solutions, standard preparations, specific antibodies, microtiter plates, and instructions for use.

30. A device for determining a protease, or its precursor after activation, in a sample, comprising a modified proenzyme as defined in claim 24.

\* \* \* \* \*